United States Patent
Boocock

(10) Patent No.: US 6,712,867 B1
(45) Date of Patent: Mar. 30, 2004

(54) PROCESS FOR PRODUCTION OF FATTY ACID METHYL ESTERS FROM FATTY ACID TRIGLYCERIDES

(75) Inventor: David Gavin Brooke Boocock, Ajax (CA)

(73) Assignee: Biox Corporation, Ontario (CA)

( * ) Notice: Subject to any disclaimer, the term of this patent is extended or adjusted under 35 U.S.C. 154(b) by 0 days.

(21) Appl. No.: 09/639,718

(22) Filed: Aug. 16, 2000

Related U.S. Application Data
(60) Provisional application No. 60/149,810, filed on Aug. 19, 1999.

(30) Foreign Application Priority Data
Aug. 18, 1999 (CA) ............................................. 2280289

(51) Int. Cl.[7] .............................................. C10L 1/18
(52) U.S. Cl. .......................... 44/389; 560/129; 554/124
(58) Field of Search .......................... 44/389; 560/129; 554/124

(56) References Cited
U.S. PATENT DOCUMENTS

| | | | | |
|---|---|---|---|---|
| 2,383,601 | A | 8/1945 | Keim ...................... | 260/410.9 |
| 4,164,506 | A | 8/1979 | Kawahara et al. .... | 260/410.9 R |
| 4,695,411 | A | 9/1987 | Stern et al. ........... | 260/410.9 R |
| 4,698,186 | A | 10/1987 | Jeromin et al. ............. | 260/421 |
| 5,525,126 | A | 6/1996 | Basu et al. .................... | 44/308 |
| 5,713,965 | A | 2/1998 | Foglia et al. ................. | 44/388 |
| 5,730,029 | A | * 3/1998 | Stoldt .......................... | 44/389 |
| 5,972,057 | A | 10/1999 | Hayafuji et al. .............. | 44/388 |
| 6,015,440 | A | * 1/2000 | Noureddini .................. | 44/388 |

FOREIGN PATENT DOCUMENTS

| | | | |
|---|---|---|---|
| AU | 4351989 | 4/1990 | |
| CA | 2131654 | 3/1996 | ........... C07C/67/02 |
| WO | 0005327 | 2/2000 | ............. C10L/1/18 |

OTHER PUBLICATIONS

"Biodiesel: Transesterification of Vegetable Oils Revisited: A Method for Increasing Base–Catalysed Methanolysis Rates", David G.B. Boocock et al., Biomass for Energy Environment Agriculture and Industry, vol. 2, 8th E. C. Conference, pp. 1192–1197 Date unknown.

"Simple, High–Efficiency Synthesis of Fatty Acid Methyl Esters from Soapstock", Michael J. Haas et al., JAOCS, vol. 77, No. 4 (2000), pp. 373–379.

"Fast Formation of High–Purity Methyl Esters from Vegetable Oils", David G.B. Boocock et al., JAOCS, vol. 75, No. 9 (1998), pp. 1167–1172.

"Zur katalytischen Umesterung fetter Oele durch alkoholische Kalilauge", Von Dr. Ing. H. Kurz, Wein, Fette und Seifen 1937, Heft 4, pp. 144–145.

"Fast One–Phase Oil–Rich Processes for the Preparation of Vegetable Oil Methyl Esters", David G.B. Boocock et al., Biomass and Bioenergy, vol. 11, No. 1, 1996, pp. 43–50.

\* cited by examiner

*Primary Examiner*—Cephia D. Toomer
(74) *Attorney, Agent, or Firm*—Webb Ziesenhiem Logsdon Orkin & Hanson, P.C.

(57) ABSTRACT

A process for the esterification of a triglyceride. The process comprises forming a single phase solution of said triglyceride in an alcohol selected from methanol and ethanol, the ratio of alcohol to triglyceride being 15:1 to 35:1. The solution further comprises a co-solvent in an amount to effect formation the single phase and a base catalyst for the esterification reaction. After a period of time, ester is recovered from the solution. Esterification is rapid and proceeds essentially to completion. The esters may be used as biofuel or biodiesel.

19 Claims, 4 Drawing Sheets

PROCESS FOR PRODUCTION OF FATTY ACID METHYL ESTERS FROM FATTY ACID TRIGLYCERIDES

This application claims benefit of Provisional Application No. 60/149,810, filed Aug. 19, 1999.

FIELD OF THE INVENTION

The present invention relates to the production of fatty acid methyl esters from fatty acid triglycerides. In particular, the invention relates to a single-phase process for the transesterification of fatty acid triglycerides with alcohol in the presence of a base catalyst.

BACKGROUND OF THE INVENTION

The transesterification of vegetable oils to form esters, and in particular, methyl esters, has received considerable attention, primarily because the esters may be used as "biofuels" or "biodiesel". Biofuels are fuels derived from renewable resources such as naturally occurring fats and oils. Such fats and oils may be obtained from a variety of plant and animals. Biodiesel relates to the specific application to diesel fuel.

The major components of an oil or fat are fatty acid triglycerides, in which three long chain fatty acid moieties are joined to one glycerol moiety by ester linkages, particularly when the fats and oils are in the form of vegetable oils. Other sources of fats and oils contain a significant proportion of fatty acids.

A number of manufacturing facilities have been built in Europe for the manufacture of biofuels, and similar facilities are planned for other countries.

The formation of vegetable oil methyl esters by the base-catalyzed reaction of triglycerides in the vegetable oil with methanol is a two-phase reaction, and is known to be slow. Methanolysis is understood to occur only in the methanol phase. Low oil concentration in methanol causes the slow reaction rate and a slow dissolving rate of the oil in the methanol causes an initiation period. As the concentration increases, the reaction rate also increases. However, the reaction rate subsequently decreases, and the reaction tends to stop before completion.

The problem of the slow reaction rate may be alleviated by the use of non-reactive co-solvents, which result in the conversion of the two-phase system into a single phase. Simple ethers, such as tetrahydrofuran (THF) and methyl-tertiarybutylether (MTBE), are particularly good co-solvents, as is described in Canadian Patent Application 2,131,654, published Mar. 9, 1996. However, the one-phase process using co-solvents still exhibits a dramatic slowing of the reaction rate. For example, in embodiments of the reaction, about 68% of the ester may be formed in the first minute, but only a total of 77% by the end of the second minute of the reaction. Molar ratios of alcohol to triglyceride of at least 4.5:1 and more preferably at least about 6:1 are disclosed, with typical ratios being in the range of 6:1 to 8:1.

The reaction is discussed by D. G. B. Boocock et al in Biomass and Bioenergy Vol. 11, No. 1 pp 43–50 (1996). Explanations for the slowing of the methanolysis reaction are stated to include possible formation of cyclic products, fall in polarity of the reaction mixture due to methanol depletion or mixing of oil, methanol and cosolvent and depletion of hydroxide ion if present.

U.S. Pat. No. 5,525,126 of Basu et al discloses esterification of mixtures of fats and oils using a calcium acetate/barium acetate catalyst. However, the method requires elevated temperature, in excess of 200° C., and elevated pressures of approximately 500 psi. Reaction times are long, being three hours. These conditions render the esterification process impractical and uneconomical for an industrial process.

U.S. Pat. No. 5,713,965 of Foglia et al. discloses use of lipases in the transesterification of triglyceride-containing substances and free fatty acids. Reaction times of 4–16 hours are required in order to obtain conversion rates of 95%, which is not practical for an industrial process.

WO 00/05327 of Ginosar et al. describes use of a "critical fluid", high temperature and pressure to effect a transesterification reaction.

Improvements in processes for the production of fatty acid methyl esters from triglycerides are required. In particular, a process for the conversion of triglycerides to the corresponding ester in a manner that is fast, essentially complete and is cost effective for both capital and operating costs is required. Such a process would offer potential as an industrial process.

The present application is directed to esterification of triglycerides in the absence of fatty acids.

SUMMARY OF THE INVENTION

Processes for the production of fatty acid methyl esters from triglycerides have now been found.

Accordingly, one aspect of the present invention provides a process for the esterification of a triglyceride, comprising:
(a) forming a single phase solution of said triglyceride, an alcohol, a base catalyst for the esterification reaction and a cosolvent at a temperature that is less than the boiling point of the solution, said alcohol being selected from the group consisting of methanol and ethanol, and mixtures thereof, and the ratio of alcohol to triglyceride being in the range of 15:1 to 35:1, the cosolvent being in an amount to effect formation of the single phase; and
(b) after a period of time, recovering ester from said solution.

In preferred embodiments of the invention, the triglyceride is selected from the group consisting of beef tallow, coconut oil, corn oil, cottonseed oil, lard, olive oil, palm oil, palm kernel oil, peanut oil, soybean oil, linseed oil, tung oil, sunflower oil, safflower oil, canola oil, rapeseed oil, sesame oil, babassu oil, perilla oil, oiticica oil, fish oils, menhaden oil, castor oil, Chinese tallow tree oil, Physic nut oil, Cuphea seed oil, microalgal oils, bacterial oils and fungal oils. Preferably, the triglyceride is soybean oil, palm oil, palm kernel oil, coconut oil or canola oil.

In a further embodiment of the invention, the cosolvent is selected from the group consisting of tetrahydrofuran, 1,4-dioxane, diethyl ether, methyltertiarybutylether and diisopropyl ether.

In another embodiment of the invention, the process is a continuous process.

BRIEF DESCRIPTION OF THE DRAWINGS

The present invention is illustrated by the embodiments shown in the drawings, in which.

DETAILED DESCRIPTION OF THE INVENTION

Figure 1:
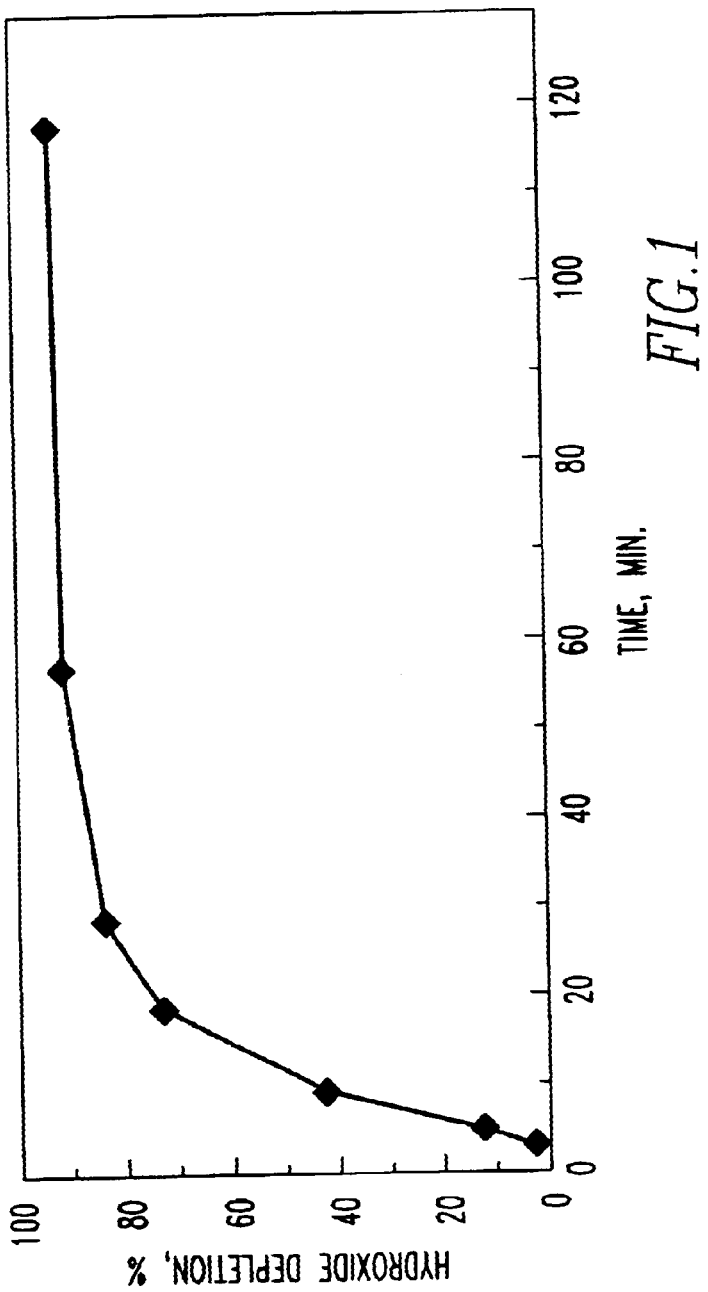
FIG. 1 is a graphical representation of depletion of hydroxide ion concentration with time during methanolysis, according to the prior art.

The present invention relates to the formation of esters from fats and oils. In particular, the present invention relates to the manufacture of such esters from triglycerides. Although the formation of methyl esters is particularly discussed herein, which is the preferred embodiment, the esterification reaction may be carried out using either methanol or ethanol, or mixtures thereof. The invention will be particularly described herein with reference to the use of methanol.

In the process of the present invention, a single phase solution of the fatty acid triglyceride is formed. The triglyceride is mixed with the alcohol viz. methanol or ethanol, or mixtures thereof, in a ratio of alcohol:triglyceride that is in the range of 15:1 to 35:1. A co-solvent is added to effect formation of the single phase solution. A base catalyst is also added. The reaction solution should contain less than about 1% by weight of water, and preferably less than 0.5% by weight of water.

The base catalyst is typically sodium hydroxide or potassium hydroxide, although the corresponding methoxides may be used. The hydroxides are preferred because of safety considerations. Other soluble or insoluble base catalysts may be used.

In the process, the catalyst dissolves and ionizes. The resultant hydroxide ion, if sodium hydroxide is the catalyst, then equilibrates with methanol to form a methoxide ion. The methoxide ion reacts with the triglyceride to cause formation of the corresponding methyl esters. The stoichiometry of the reaction of triglycerides with methanol requires 3 moles of alcohol for each mole of fatty acid triglyceride. The reaction proceeds in a step-wise manner, through the diglyceride and monoglyceride intermediates, both of which involve equilibrium reactions. An excess of alcohol has been used in the prior art, conventionally in ratios of alcohol to triglyceride of 6:1 to 8:1, as is noted above. It would be expected from the $pK_a$ of methanol that any increase in the amount of alcohol would lower the rate of conversion by diluting the methoxide ion concentration.

It has now been found that addition of methanol, with an appropriate amount of co-solvent, in molar ratios of methanol to fatty acid triglyceride of 15:1 to 35:1 results in substantial increases in both conversion and rate of conversion of triglyceride to methyl ester. Preferred molar ratios are in the range of 20:1 to 30:1, and most preferably in the range of 25:1 to 30:1. The increased conversion and rate of conversion are illustrated in the Examples herein. Moreover, it has been found that the reaction does not terminate or slow down at low degrees of conversion, but can proceed to in excess of 99% conversion, as exemplified herein.

The alcohol used in the transesterification processes of the present invention is methanol or ethanol, or a mixture thereof, with methanol being most preferred. Methanol boils at 64.5° C. and ethanol boils at 78.3° C.

A wide range of oils and fats derived from animals and plants may be used as the source of fatty acid triglycerides. Examples include beef tallow, coconut oil, corn oil, cottonseed oil, lard, olive oil, palm oil, palm kernel oil, peanut oil, soybean oil, linseed oil, tung oil, sunflower oil, safflower oil, canola oil, rapeseed oil, sesame oil, babassu oil, perilla oil, oiticica oil, fish oils, menhaden oil, castor oil, Chinese tallow tree oil, Physic nut oil, Cuphea seed oil, microalgal oils, bacterial oils and fungal oils. While a range of vegetable oils may be used in the process of the present invention, it is particularly applicable to vegetable oils having at least 16 carbon atoms i.e. triglycerides with fatty acid moieties that are $C_{16}$ or higher.

The most preferred sources of fatty acid triglycerides are soybean oil, palm oil, palm kernel oil, coconut oil and canola oil, because they are inexpensive and available in large quantities. However, other fats and oils are also suitable for the production of biofuel from triglycerides, including the fats and oils listed above.

A cosolvent is added in at least an amount sufficient to form a single phase solution of the alcohol, fatty acid triglyceride and cosolvent. The cosolvent is preferably completely miscible with both the alcohol and the source of fatty acid triglyceride. The cosolvent preferably has a boiling point of less than about 120° C. to facilitate solvent removal after the reaction is complete. More preferably, the cosolvent has a boiling point similar to that of the alcohol. Preferred cosolvents are cyclic ethers, which have a hydrophilic oxygen atom capable of forming hydrogen bonds with water and alcohols, and a hydrophobic hydrocarbon portion capable of solubilizing many organic compounds. Examples of cosolvents are cyclic ethers such as tetrahydrofuran (THF) and 1,4-dioxane, diethyl ether, methyltertiarybutylether and diisopropyl ether.

The cosolvent is preferably anhydrous. Larger amounts of cosolvent can be added than are required to solubilize the oil or fat with satisfactory results.

The most preferred cosolvent is THF, especially for methanolysis, as un-reacted methanol and THF may be co-distilled and recycled at the end of the reaction. The amount of cosolvent needed depends on the particular source of fatty acid triglyceride, the alcohol being used and the co-solvent.

The reaction is carried out below the lower of the boiling points of the solvent and cosolvent. For methanolysis in the presence of THF (b.p. 67°), the temperature should be not more than about 65° C. viz. the boiling point of methanol. However, for ethanolysis using ethanol (b.p. 78° C.) in the presence of THF (b.p. 67° C.), the temperature should be not more than about 67° C. A range of temperature may be used. For instance, temperatures of less than 65° C. may be used, including temperatures at or below ambient temperature (15° C.). However, higher temperatures do increase the rate of reaction, and preferred temperatures are at least 50° C., especially at least 60° C., and preferably 60–65° C. The reaction may be carried out without substantial agitation of the reaction mixture.

The base catalyst should be substantially moisture free, and preferably stored under substantially anhydrous conditions. Prolonged contact of base catalysts with air should also be avoided, because water and carbon dioxide tend to diminish the effectiveness of the catalyst.

The base catalyst is preferably added to the reaction mixture in the form of a solution, either in the alcohol being used in the reaction or in an alcohol/cosolvent mixture. Heat and stirring may be necessary to dissolve the catalyst. The alcoholic solution of base catalyst is preferably added quickly to the reaction mixture.

As exemplified herein, conversion of the triglyceride to the ester is rapid, and a high conversion may be obtained in minutes, depending on the reactants and reaction conditions.

After completion of the reaction, the alcohol e.g. methanol, remaining in the reaction mixture and the cosolvent e.g. tetrahydrofuran (THF) are separated, e.g. by distillation or flashing off. Such distillation or flashing off may be carried out either at atmospheric pressure or at reduced pressure. On removal of the alcohol and cosolvent, a glycerol phase is formed. It has been found that the alcohol and cosolvent may be co-distilled prior to separation of the glycerol layer without any substantial amount of reverse transesterification.

Separation of the glycerol phase may be effected, for instance, under gravity or more preferably by centrifugation.

The remaining layer of the reaction mixture is primarily comprised of fatty acid esters. The fatty acid esters that are obtained typically have boiling points that are substantially higher than those of either the cosolvent or the alcohol.

Hydroxide ion remaining after the reaction may be neutralized by the addition of acid prior to distillation of the cosolvent and excess alcohol.

As exemplified herein, high yields viz. greater than 99%, may be obtained using the process of the present invention. If the product obtained contains trace amounts of residual mono- or di-glycerides, such residual amounts may be removed. One method of removal is use of an adsorbent. Examples of adsorbents include alumina, silica gel and other silicon-based adsorbents e.g. Fluorosil™ adsorbent. In an embodiment of the invention, the product obtained is passed through a column of the absorbent.

The process of the present invention may be operated as a batch process. However, it is preferred to operate the process as a continuous process. Such a continuous process may be operated over a range of temperatures, as noted above, including ambient temperature and elevated temperatures. Thus, in some parts of the world, the process of the invention is conveniently operated outdoors at ambient temperatures. In cooler climates, the process may be operated at conventional indoor temperatures.

In a continuous industrial process, it is preferred to co-distill the cosolvent and excess alcohol at the end of the reaction, for recycle. The catalyst may then be dissolved in the cosolvent/alcohol solution and added to a reaction vessel containing the source of triglyceride. Additional alcohol and/or cosolvent would be added as required. After the reactants have been mixed in the reaction vessel, stirring may be discontinued.

It is preferred that the purified esters contain no more than 0.25% by weight of total glycerol moieties (including mono- and diglycerides) and no more than 0.03% by weight of free glycerol. Glycerol present in the biofuel can clog injectors of diesel engines. Glycerol is a valuable by-product of the reaction and has many uses such as in resins, pharmaceuticals, soaps, and foods.

As noted in Canadian patent application No. 2,131,654, free fatty acids are particularly troublesome components of fats and oils, particularly where the transesterification reaction is catalyzed with a base. Under such conditions, free fatty acids are neutralized to form soaps. As noted above, the present invention is directed to the esterification of fatty acid triglycerides substantially in the absence of fatty acids.

The process of the present invention gives rapid conversion of fatty acid triglycerides to fatty acid esters, which have a variety of uses. The particularly preferred use is as a biofuel or biodiesel.

The ASTM standard for biodiesel that is currently being evaluated includes a requirement for total glycerol of a maximum of 0.40% by weight. For this calculation, glycerol that is in the form of a mono- (MG), di- (DG) or triglyceride (TG) must be converted to the corresponding amounts of glycerol. The conversion factors vary with the particular moieties of the vegetable oil. For soybean oil, the conversion factors to amount of glyerol are approximately 0.25 for monoglyceride, 0.14 for diglyceride and 0.10 for triglyceride. German biodiesel standard DIN V 51606 imposes an upper limit of 0.23% (wt) of glycerol.

The present invention is illustrated by the following examples:

EXAMPLE I

This example illustrates the transesterification of vegetable oils viz. coconut oil and soybean oil, using a 6:1 molar ratio of methanol to oil. Thus, this example illustrates the prior art as represented by Canadian Patent Application 2 131 654.

The soybean oil was a food-grade product and was obtained as President's Choice™, Sunfresh Ltd., Toronto, Ontario, Canada. Solvents were as follows: methanol (anhydrous, 99+%), tetrahydrofuran (anhydrous, 99+%). methyltertiary butyl ether (anhydrous, 99+%), bis (trimethylsilyl) trifluoroacetamide (BSTFA, 99+%), pyridine (anhydrous 99+%. Analytical grade sodium hydroxide (98%), concentrated hydrochloric acid, and anhydrous sodium sulfate were obtained from BDH Inc. (Toronto, Ontario, Canada).

Gas chromatography (GC) analyses of transesterified methylated products were performed on a Hewlett-Packard (Palo Alto, Calif.) 5880A series gas chromatograph equipped with an on-column injector, a flame-ionization detector (FID) and a BD-1 fused-silica capillary column (2 m×0.25 mm i.d.) coated with 0.25 $\mu$m film of 100% polymethyl siloxane.

For transesterification of soybean oil, soybean oil (100 g) and anhydrous THF (45 mL) were placed in a 500-mL flat-bottom flask equipped with a magnetic stirrer and the mixture was stirred. Sodium hydroxide [1.0 g (1.0 wt % with respect to soybean oil)] solution in methanol [28 mL (6:1 methanol-to-oil)] was then added and the stirring was continued for an additional 20 s. Samples of the reaction mixture were taken at 3, 5, 10, 20, 30, 60 and 120 minutes and quenched immediately into 125-mL Erlenmeyer flasks containing water (20 mL). The ester remained in the upper organic layer in the reaction mixture, thus allowing titration of the hydroxide ion in the water phase.

Anhydrous sodium sulfate was added to each of the vials to absorb the trace amount of moisture. The samples were then derivatized for GC analyses. The derivatization of the organic material was necessary in order to determine the amount of mono-and diglycerides present in the final product by GC. Mono-and diglycerides are sufficiently volatile for GC analysis: the addition of BSTFA reagent made them more volatile so that they could be detected by the GC.

For derivatization, anhydrous pyridine (0.4 mL) and BSTFA reagent (0.2 mL) were added to each 20-mL vial containing transesterified product (100 mg). The vials were then capped, shaken and placed on a water bath at 65° C. for 20 min. with occasional stirring. After heating, the samples were removed from the water bath, cooled to room temperature and diluted using THF (4.4 mL). The samples were then injected into the gas chromatograph to obtain a profile of the conversion of methyl ester with respect to time.

The change in hydroxide concentration in the one-phase methanolysis reaction was measured directly at room temperature (23° C.). In addition to the above, a number of transesterification reactions were carried out using soybean oil, methanol, and four different concentrations of sodium hydroxide catalyst (1.1, 1.3, 1.4, and 2.0 wt %). All other experimental conditions including the methanol-to-soybean oil molar ratio (6:1) were the same as described above for soybean oil.

Figure 2:
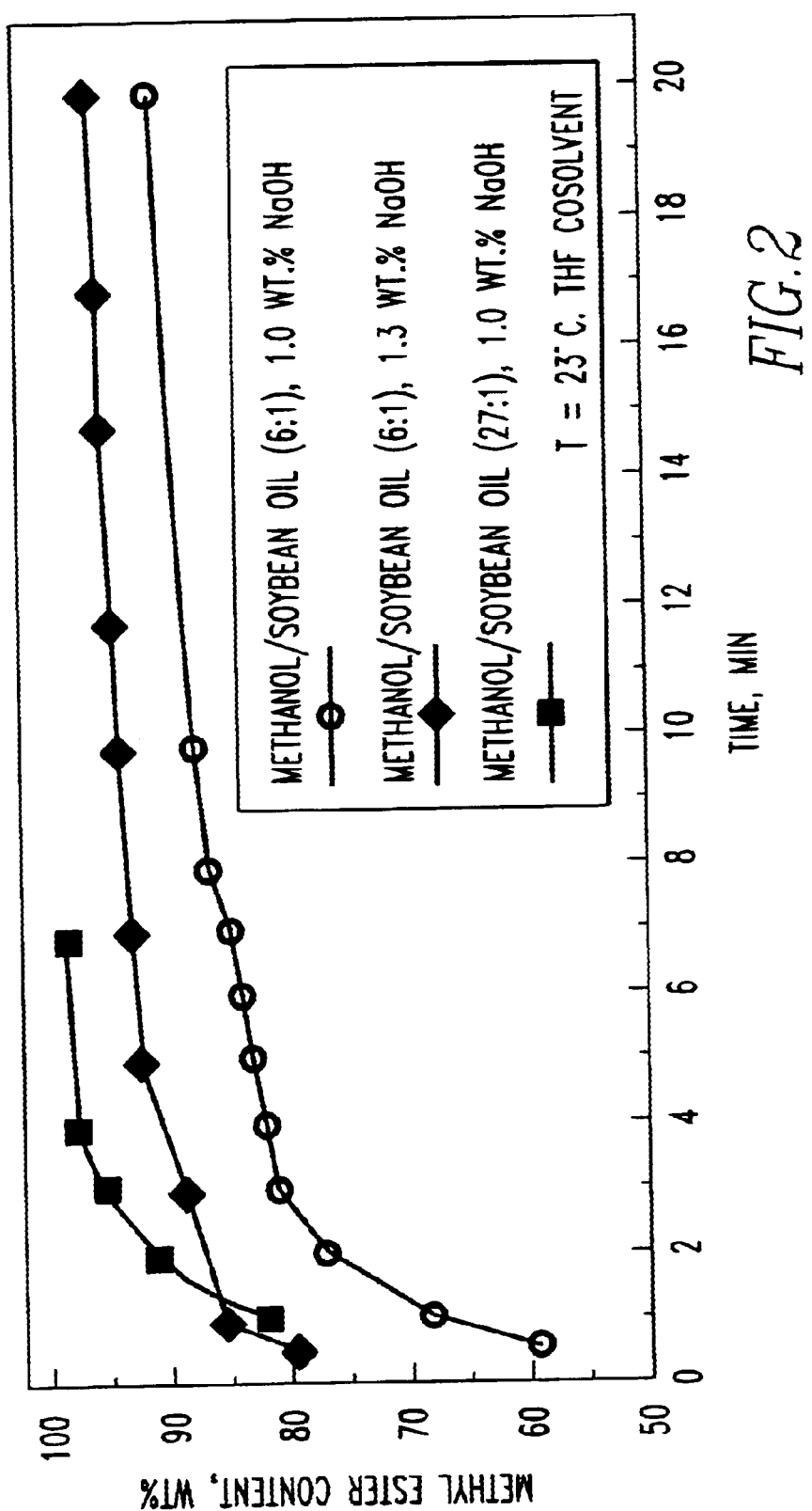
FIG. 2 is a graphical representation of a one-phase methanolysis of soybean and coconut oils, according to the prior art and to the present invention.

The results obtained are shown in FIGS. 1–2. A typical hydroxide depletion curve for the one-phase methanolysis of soybean oil at 23° C. (6:1 methanol/oil molar ratio and 1.0 wt % sodium hydroxide based on the oil) is shown in FIG. 1. Methyl ester production for soybean oil is shown in FIG. 2. Results for soybean oil in which 1.3 wt % sodium hydroxide was used, are also shown in FIG. 2.

Using the above procedures, a comparison of the reaction was made using a methanol/soybean ratio of 8:1 with a ratio of 6:1. It was found that the reaction at a molar ratio of 8:1 provided an ester content after one hour of 97.5 wt %, compared to 93.7 wt % for a 6:1 molar ratio. However, after four hours the ester contents were essentially the same.

EXAMPLE II

To illustrate the present invention, a number of experiments were also conducted using higher methanol-to-soybean oil molar ratio (25:1, 27:1, 28:1, 35:1, and 40:1) than the conventional 6:1 ratio illustrated in Example I. 1.0 wt % sodium hydroxide was used as catalyst.

The amount of THF needed to obtain the mixture in a single phase in the different methanol-to-oil molar ratio combinations was determined by a cloud point method. The ratios are shown in Table 1.

TABLE 1

Volumes of Methanol and Tetrahydrofuran (THF) Used for Different Molar Ratios of Methanol to Soybean Oil[1]

| Molar Ratio | Volume of methanol (mL) | Volume of THF (mL) |
| --- | --- | --- |
| 25:1 | 23.3 | 20.0 |
| 27:1 | 25.2 | 22.0 |
| 28:1 | 26.2 | 25.0 |
| 35:1 | 32.8 | 26.0 |
| 40:1 | 37.3 | 28.0 |

[1]Volume of oils is 23 mL in all cases.

The reaction procedure of Example I was repeated, except for the ratio of methanol to triglyceride and the amount of co-solvent.

The results obtained are shown in Table 2. Table 2 shows the results from transesterification reactions of soybean oil involving higher methanol-to-oil molar ratios than the conventional 6:1 ratio. These results are further illustrated in FIG. 2.

TABLE 2

Composition of Methyl Esters in the Products Obtained from Transesterification Reactions of Soybean Oil with Methanol Using Different Methanol/Oil Molar Ratios and 1.0 wt % NaOH Catalyst

| Time (min.) | Methyl esters (%) at different methanol:oil molar ratios | | | | |
| --- | --- | --- | --- | --- | --- |
|  | 25:1 | 27:1 | 28:1 | 35:1 | 40:1 |
| 1 | 83.3 | 82.0 | 80.6 | 73.6 | 63.7 |
| 2 | 89.3 | 90.9 | 89.5 | 88.2 | 79.7 |
| 3 | 90.2 | 95.3 | 95.1 | 91.8 | 86.2 |
| 4 | 91.3 | 98.2 | 97.1 | 95.7 | 95.5 |
| 5 | 94.7 | 98.3 | 98.0 | 96.2 | 95.0 |
| 7 | NA[2] | 99.4 | 99.2 | NA | NA |

[2]NA = Not available

The results of Table 2 show that increasing the methanol to oil ratio into the range of 15:1 to 35:1 and particularly in the range of 25:1 to 30:1 resulted in a substantial increase in the amount of methyl ester. In particular, results at 27:1 and 28:1 showed 99.4 and 99.2% conversion, respectively, in a period of only 7 minutes. This is a higher conversion in substantially shorter reaction times than obtained using the procedures of the prior art as illustrated in Example I.

EXAMPLE III

This example illustrates a continuous process of the present invention.

A solution of soybean oil, methanol and tetrahydrofuran (THF) in a volumetric ratio of 1.0:0.974:0.957 was pumped from a reservoir through a polypropylene tube (0.05 cm ID) to a T-joint, using two Pharmacia-Biotech P-500 pumps operating in parallel. A third pump delivered a solution of sodium hydroxide (catalyst) in methanol (7.2 g/100 mL) to the T-joint. The ratio of the flow rates of the soybean oil solution and sodium hydroxide solution was 24.05:1, which provided a molar ratio of methanol:oil of 27:1 and a sodium hydroxide concentration of 1.0 wt %, based on the amount of oil.

The resultant solution was passed through further polypropylene tubing to a static mixer, which was in the form of a glass tube (20 cm long×0.5 cm ID) packed with glass beads (0.1 cm diameter). The void (mixing) space in the static mixer was 0.46 cm³. The solution was then passed to a glass reactor in the form of glass tubing (6.89 m, 0.5 cm ID) coiled in 14.5 helical loops. The flow rates of the soybean solution and sodium hydroxide solution were 842 mL/hour and 35 mL/hour, respectively, which provided a total residence time after mixing of 10 min 3 sec (603 s).

Samples were collected from the outlet of the reactor, commencing at a time of 13 minutes (residence time plus three minutes) after the reaction was started. The samples were immediately quenched in 1 N HCl. The samples were then derived and analyzed by gas chromatography using the procedure of Example I.

The results obtained showed that the monoglyceride content of the samples varied from 0.35 to 0.65 wt % and the methyl ester content varied from 99.35 to 99.65 wt % during the run. The average composition of the samples was 99.46 wt % methyl ester and 0.54 wt % monoglyceride. No diglycerides or triglycerides were detected.

EXAMPLE IV

This example illustrates the present invention using ethanol as the alcohol and potassium hydroxide as the base catalyst. The example also illustrates the use of an adsorbent.

Sunflower oil (Unico Inc. 20.0 g, 22.0 mL) was placed in a 150 mL round-bottom flask equipped with a magnetic stirrer. Anhydrous ethanol (29.2 mL) and tetrahydrofuran (THF) (8.5 mL) were added to form a homogenous phase. A solution of potassium hydroxide in ethanol (0.28 g in 4.0 mL) was added and the mixture stirred for an additional 20 seconds. This gave an ethanol/oil molar ratio of 25:1 and a catalyst concentration of 1.4 wt % with respect to the oil (equivalent to 1.0 wt % NaOH). After a further ten minutes, sodium hydrogen sulphate monohydrate (0.78 g) was added to stop the reaction. The potassium sulphate obtained was filtered off.

Ethanol and THF were removed on a Buchi Rotavapour at approximately 20 mm Hg pressure. The mixture was then cooled and the glycerol layer was allowed to settle. The upper ester layer was removed, washed and dried. This product contained 98.1% ethyl ester and 1.9 wt % monoglyceride.

The product of ethyl ester and monoglyceride was dissolved in hexane (20 mL) and fed to the top of a column of silica gel (20.0 g) in a column (18 cm high×3 cm diameter) that had been packed using hexane solvent. Hexane was passed through the column at a flow rate of 1–2 mL per minute. It was determined that most of the ester had emerged from the column after 40 mL of hexane had passed through it. After removal of the hexane, the monoglyceride content of the ethyl ester product had fallen to 0.2–0.3 wt %.

EXAMPLE V

This example illustrates the effect of molar ratio on the conversion of triglyceride to ester, using ethanol as the alcohol.

The procedure of Example IV was repeated using various molar ratios of ethanol to fatty acid triglyceride (sunflower oil). Conversion with time was investigated at the various molar ratios, at room temperature and using 1.4 wt % KOH as catalyst.

Figure 3:
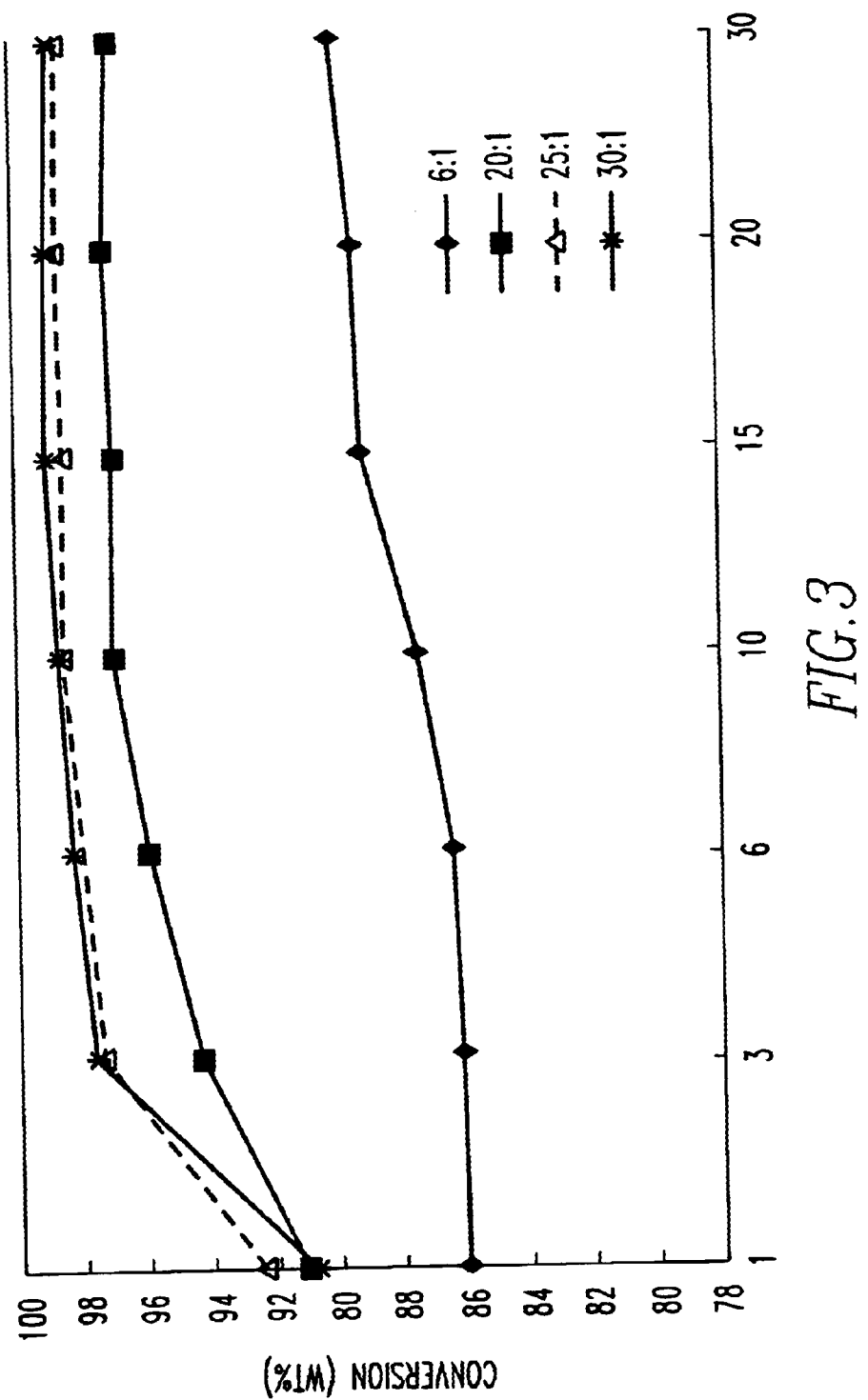
FIG. 3 is a graphical representation of effects of molar ratio on ethanolysis.

The results obtained are shown in FIG. 3.

An increase in molar ratio from 6:1 to 20:1 resulted in a substantial increase in conversion. Further increases to 25:1 and 30:1 caused additional increases in conversion, and an increase in the rate of the reaction as may be noted by the results obtained after 3 minutes.

EXAMPLE VI

This example illustrates the effect of temperature on the conversion of triglyceride to ester, using ethanol as the alcohol. The procedure of Example IV was repeated using a molar ratio of ethanol to fatty acid triglyceride (sunflower oil) of 25:1. Conversion with time was investigated at various temperatures and using 1.4 wt % KOH as catalyst. The temperatures used were as follows: 23° C., 40° C. and 60° C.

Figure 4:
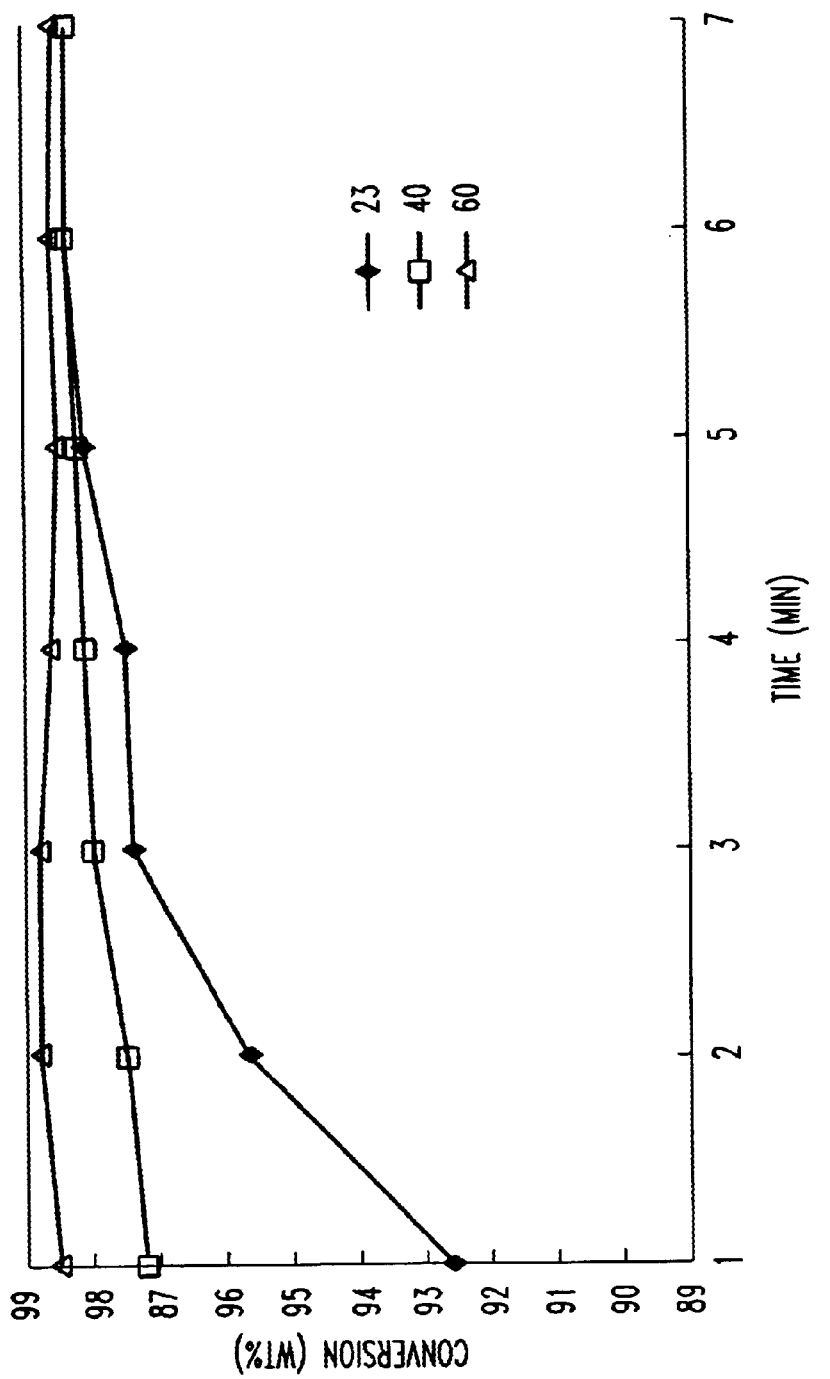
FIG. 4 is a graphical representation of effects of temperature on ethanolysis.

The results obtained are shown in FIG. 4.

Increasing the temperature from 23° C. to 40° C. resulted in substantial increases in conversion, especially in the period of 1–3 minutes. A further increase was obtained at 60° C. After a reaction time of five minutes, the conversion was substantially the same at all temperatures.

What is claimed is:

1. A process for the esterification of triglyceride, comprising forming a single phase solution of said triglyceride, an alcohol, a base catalyst for the esterification reaction and a cosolvent at a temperature that is less than the boiling point of the solution, said alcohol being selected from the group consisting of methanol and ethanol, and mixtures thereof, and the ratio of alcohol to triglyceride being in the range of 15:1 to 35:1, the cosolvent being in an amount sufficient to effect formation of the single phase; permitting esterification to occur in said solution and recovering ester from said solution.

2. The process of claim 1 in which the solution contains less than 1% by weight of water.

3. The process of claim 2 in which the solution contains less than 0.5% by weight of water.

4. The process of claim 2 in which the alcohol is methanol.

5. The process of claim 2 in which the alcohol is ethanol.

6. The process of claim 2 in which the alcohol is a mixture of ethanol and methanol.

7. The process of claim 2 in which the base catalyst is selected from sodium hydroxide and potassium hydroxide.

8. The process of claim 2 in which the molar ratio of alcohol to triglyceride is in the range of 20:1 to 30:1.

9. The process of claim 8 in which the molar ratio of alcohol to triglyceride is in the range of 25:1 to 30:1.

10. The process of claim 8 in which the triglyceride has fatty acid moieties that are $C_{16}$ or higher.

11. The process of claim 8 in which the triglyceride is selected from the group consisting of beef tallow, coconut oil, corn oil, cottonseed oil, lard, olive oil, palm oil, palm kernel oil, peanut oil, soybean oil, linseed oil, tung oil, sunflower oil, safflower oil, canola oil, rapeseed oil, sesame oil, babassu oil, perilla oil, oiticica oil, fish oils, menhaden oil, castor oil, Chinese tallow tree oil, Physic nut oil, Cuphea seed oil, microalgal oils, bacterial oils and fungal oils.

12. The process of claim 8 in which the cosolvent is a cyclic ether.

13. The process of claim 8 in which the cosolvent is selected from the group consisting of tetrahydrofuran, 1,4-dioxane, diethyl ether, methyltertiarybutylether and diisopropyl ether.

14. The process of claim 8 in which the temperature is in the range of from 15° C. to 65° C.

15. The process of claim 8 in which the temperature is at least 50° C.

16. The process of claim 15 in which the temperature is at least 60° C.

17. The process of claim 8 in which ester is recovered in a yield of at least 99%.

18. The process of claim 9 in which the triglyceride is selected from the group consisting of soybean oil, palm oil, palm kernel oil, coconut oil and canola oil.

19. The process of claim 1 in the form of a continuous process.

* * * * *